(12) United States Patent
Hawkins et al.

(10) Patent No.: US 9,180,280 B2
(45) Date of Patent: Nov. 10, 2015

(54) DRUG DELIVERY SHOCKWAVE BALLOON CATHETER SYSTEM

(75) Inventors: Daniel Hawkins, Fremont, CA (US); John M. Adams, Snohomish, WA (US)

(73) Assignee: SHOCKWAVE MEDICAL, INC., Fremont, CA (US)

( * ) Notice: Subject to any disclaimer, the term of this patent is extended or adjusted under 35 U.S.C. 154(b) by 880 days.

(21) Appl. No.: 12/581,295

(22) Filed: Oct. 19, 2009

(65) Prior Publication Data

US 2010/0114065 A1    May 6, 2010

Related U.S. Application Data

(60) Provisional application No. 61/111,196, filed on Nov. 4, 2008.

(51) Int. Cl.
| | | |
|---|---|---|
| *A61M 25/10* | (2013.01) | |
| *A61B 17/22* | (2006.01) | |
| *A61B 17/3207* | (2006.01) | |
| *A61B 17/225* | (2006.01) | |

(52) U.S. Cl.
CPC ........ *A61M 25/1006* (2013.01); *A61B 17/2202* (2013.01); *A61B 17/22022* (2013.01); *A61B 17/320725* (2013.01); *A61M 25/104* (2013.01); *A61B 17/22029* (2013.01); *A61B 17/2256* (2013.01); *A61B 2017/22024* (2013.01); *A61B 2017/22082* (2013.01); *A61B 2017/22088* (2013.01); *A61M 2025/105* (2013.01); *A61M 2025/1086* (2013.01)

(58) Field of Classification Search
CPC .......... A61M 25/104; A61M 25/1006; A61M 2025/1086; A61M 2025/105; A61M 2025/1075; A61B 17/22022; A61B 17/320725; A61B 17/2202; A61B 17/22029; A61B 17/2256; A61B 2017/22024; A61B 2017/22088
USPC ....................... 604/103.02, 22, 509
See application file for complete search history.

(56) References Cited

U.S. PATENT DOCUMENTS 3,785,382 A    1/1974   Schmidt et al.
3,902,499 A    9/1975   Shene (Continued)

FOREIGN PATENT DOCUMENTS

DE    3038445 A1    5/1982
EP    0442199 A2    8/1991

(Continued)

OTHER PUBLICATIONS

International Search Report received for PCT Patent Application No. PCT/US2009/047070, mailed on Jan. 19, 2010, 4 pages.

(Continued)

*Primary Examiner* — Bhisma Mehta
*Assistant Examiner* — Jenna Zhang
(74) *Attorney, Agent, or Firm* — Morrison & Foerster LLP

(57) ABSTRACT

A catheter comprises an elongated carrier and a balloon carried by the carrier in sealed relation thereto. The balloon has an outer surface and is arranged to receive a fluid therein that inflates the balloon. The catheter further comprises a shock wave generator within the balloon that forms mechanical shock waves within the balloon, and a medicinal agent carried on the outer surface of the balloon. The medicinal agent is releasable from the balloon by the shock waves.

23 Claims, 8 Drawing Sheets

(56) References Cited

U.S. PATENT DOCUMENTS

| | | | |
|---|---|---|---|
| 4,027,674 A | 6/1977 | Tessler et al. | |
| 4,662,126 A | 5/1987 | Malcolm | |
| 4,685,458 A | 8/1987 | Leckrone | |
| 4,809,682 A | 3/1989 | Forssmann et al. | |
| 4,900,303 A | 2/1990 | Lemelson | |
| 5,009,232 A | 4/1991 | Hassler et al. | |
| 5,057,103 A | 10/1991 | Davis | |
| 5,078,717 A | 1/1992 | Parins et al. | |
| 5,102,402 A | 4/1992 | Dror et al. | |
| 5,103,804 A | 4/1992 | Abele et al. | |
| 5,152,767 A | 10/1992 | Sypal et al. | |
| 5,152,768 A | 10/1992 | Bhatta | |
| 5,176,675 A | 1/1993 | Watson et al. | |
| 5,246,447 A | 9/1993 | Rosen et al. | |
| 5,281,231 A | 1/1994 | Rosen et al. | |
| 5,324,255 A | 6/1994 | Passafaro et al. | |
| 5,336,234 A | 8/1994 | Vigil et al. | |
| 5,368,591 A | 11/1994 | Lennox et al. | |
| 5,395,335 A | 3/1995 | Jang | |
| 5,417,208 A | 5/1995 | Winkler | |
| 5,425,735 A | 6/1995 | Rosen et al. | |
| 5,472,406 A | 12/1995 | de la Torre et al. | |
| 5,582,578 A | 12/1996 | Zhong et al. | |
| 5,603,731 A | 2/1997 | Whitney | |
| 5,609,606 A | 3/1997 | O'Boyle | |
| 5,662,590 A | 9/1997 | de la Torre et al. | |
| 5,893,840 A | 4/1999 | Hull et al. | |
| 5,931,805 A | 8/1999 | Brisken | |
| 6,007,530 A | 12/1999 | Doernhoefer et al. | |
| 6,033,371 A | 3/2000 | Torre et al. | |
| 6,083,232 A | 7/2000 | Cox | |
| 6,146,358 A | 11/2000 | Rowe | |
| 6,210,408 B1 | 4/2001 | Chandrasekaran et al. | |
| 6,217,531 B1 | 4/2001 | Reitmajer | |
| 6,277,138 B1 | 8/2001 | Levinson et al. | |
| 6,287,272 B1* | 9/2001 | Brisken et al. | 604/22 |
| 6,352,535 B1 | 3/2002 | Lewis et al. | |
| 6,367,203 B1 | 4/2002 | Graham et al. | |
| 6,371,971 B1 | 4/2002 | Tsugita et al. | |
| 6,398,792 B1 | 6/2002 | O'Connor | |
| 6,406,486 B1 | 6/2002 | de la Torre et al. | |
| 6,514,203 B2 | 2/2003 | Bukshpan | |
| 6,524,251 B2 | 2/2003 | Rabiner et al. | |
| 6,589,253 B1 | 7/2003 | Cornish et al. | |
| 6,607,003 B1 | 8/2003 | Wilson | |
| 6,638,246 B1 | 10/2003 | Naimark et al. | |
| 6,652,547 B2 | 11/2003 | Rabiner et al. | |
| 6,736,784 B1 | 5/2004 | Menne et al. | |
| 6,740,081 B2 | 5/2004 | Hilal | |
| 6,755,821 B1 | 6/2004 | Fry | |
| 6,939,320 B2 | 9/2005 | Lennox | |
| 6,989,009 B2 | 1/2006 | Lafontaine | |
| 7,066,904 B2 | 6/2006 | Rosenthal et al. | |
| 7,241,295 B2 | 7/2007 | Maguire | |
| 7,569,032 B2 | 8/2009 | Naimark et al. | |
| 8,556,813 B2 | 10/2013 | Cioanta et al. | |
| 8,728,091 B2 | 5/2014 | Hakala et al. | |
| 2001/0044596 A1 | 11/2001 | Jaafar | |
| 2002/0177889 A1 | 11/2002 | Brisken et al. | |
| 2003/0004434 A1 | 1/2003 | Greco et al. | |
| 2003/0176873 A1 | 9/2003 | Chernenko et al. | |
| 2003/0229370 A1 | 12/2003 | Miller | |
| 2004/0044308 A1* | 3/2004 | Naimark et al. | 604/103 |
| 2004/0097996 A1 | 5/2004 | Rabiner et al. | |
| 2004/0254570 A1 | 12/2004 | Hadjicostis et al. | |
| 2005/0015953 A1 | 1/2005 | Keidar | |
| 2005/0021013 A1 | 1/2005 | Visuri et al. | |
| 2005/0251131 A1 | 11/2005 | Lesh | |
| 2006/0004286 A1 | 1/2006 | Chang et al. | |
| 2006/0184076 A1 | 8/2006 | Gill et al. | |
| 2006/0190022 A1* | 8/2006 | Beyar et al. | 606/192 |
| 2007/0088380 A1 | 4/2007 | Hirszowicz et al. | |
| 2007/0239082 A1 | 10/2007 | Schultheiss et al. | |
| 2007/0239253 A1* | 10/2007 | Jagger et al. | 623/1.11 |
| 2007/0244423 A1 | 10/2007 | Zumeris et al. | |
| 2008/0097251 A1 | 4/2008 | Babaev | |
| 2008/0188913 A1 | 8/2008 | Stone et al. | |
| 2009/0041833 A1* | 2/2009 | Bettinger et al. | 424/450 |
| 2009/0247945 A1 | 10/2009 | Levit et al. | |
| 2009/0254114 A1 | 10/2009 | Hirszowics et al. | |
| 2009/0312768 A1 | 12/2009 | Hawkins et al. | |
| 2010/0016862 A1 | 1/2010 | Hawkins et al. | |
| 2010/0036294 A1 | 2/2010 | Mantell et al. | |
| 2010/0114020 A1 | 5/2010 | Hawkins et al. | |
| 2010/0121322 A1 | 5/2010 | Swanson | |
| 2010/0305565 A1 | 12/2010 | Truckai et al. | |
| 2011/0034832 A1 | 2/2011 | Cioanta et al. | |
| 2011/0118634 A1 | 5/2011 | Golan | |
| 2011/0166570 A1 | 7/2011 | Hawkins et al. | |
| 2011/0257523 A1 | 10/2011 | Hastings et al. | |
| 2011/0295227 A1 | 12/2011 | Hawkins et al. | |
| 2012/0071889 A1 | 3/2012 | Mantell et al. | |
| 2012/0095461 A1 | 4/2012 | Herscher et al. | |
| 2012/0203255 A1 | 8/2012 | Hawkins et al. | |
| 2012/0221013 A1 | 8/2012 | Hawkins et al. | |
| 2013/0030431 A1 | 1/2013 | Adams | |
| 2013/0030447 A1 | 1/2013 | Adams | |
| 2013/0150874 A1 | 6/2013 | Kassab | |
| 2014/0046229 A1 | 2/2014 | Hawkins et al. | |
| 2014/0052147 A1 | 2/2014 | Hakala et al. | |
| 2014/0074111 A1 | 3/2014 | Hakala et al. | |
| 2014/0243820 A1 | 8/2014 | Adams et al. | |
| 2014/0243847 A1 | 8/2014 | Hakala et al. | |

FOREIGN PATENT DOCUMENTS

| | | |
|---|---|---|
| EP | 571306 A1 | 11/1993 |
| JP | 62-275446 A | 11/1987 |
| JP | 6-125915 A | 5/1994 |
| JP | 7-47135 A | 2/1995 |
| JP | 10-99444 A | 4/1998 |
| JP | 10-513379 A | 12/1998 |
| JP | 2002-538932 A | 11/2002 |
| JP | 2004-81374 A | 3/2004 |
| JP | 2005-95410 A | 4/2005 |
| JP | 2005-515825 A | 6/2005 |
| JP | 2006-516465 A | 7/2006 |
| WO | 96/24297 A1 | 8/1996 |
| WO | 2004/069072 A2 | 8/2004 |
| WO | 2006/127158 A2 | 11/2006 |
| WO | 2007/149905 A2 | 12/2007 |
| WO | 2009/121017 A1 | 10/2009 |
| WO | 2009/152352 A2 | 12/2009 |
| WO | 2010-014515 A2 | 2/2010 |
| WO | 2011/143468 A2 | 11/2011 |
| WO | 2013/059735 A1 | 4/2013 |

OTHER PUBLICATIONS

International Preliminary Report on Patentability received for PCT Patent Application No. PCT/US2011/047070, mailed on Feb. 21, 2013, 7 pages.

International Written Opinion received for PCT Patent Application No. PCT/US2011/047070, mailed on May 1, 2012, 5 pages.

International Search Report received for PCT Patent Application No. PCT/US2012/023172, mailed on Sep. 28, 2012, 3 pages.

International Search Report and Written Opinion received for PCT Patent Application No. PCT/US2013/031805 mailed on May 20, 2013, 13 pages.

Adams et al., U.S. Appl. No. 13/534,658, filed Jun. 27, 2012, titled "Shock Wave Balloon Catheter with Multiple Shock Wave Sources". (Copy not attached.).

Adams et al., U.S. Appl. No. 13/777,807, filed Feb. 26, 2013, titled "Shock Wave Catheter System with ARC Preconditioning". (Copy not attached.).

Hakala et al., U.S. Appl. No. 13/615,107, filed Sep. 13, 2012, titled "Shockwave Catheter System with Energy Control". (Copy not attached.).

Hakala et al., U.S. Appl. No. 13/831,543, filed Mar. 14, 2013, titled "Low Profile Electrodes for an Angioplasty Shock Wave Catheter", 52 pages. (Copy not attached.).

(56) References Cited

OTHER PUBLICATIONS

Non Final Office Action received for U.S. Appl. No. 12/482,995, mailed on Jul. 12, 2013, 11 pages.
International Preliminary Report on Patentability received for PCT Patent Application No. PCT/US2012/023172, mailed on Aug. 15, 2013, 6 pages.
Office Action received for Australian Patent Application No. 2009257368, issued on Jul. 31, 2013, 4 pages.
Office Action received for Japanese Patent Application No. 2011-513694, mailed on Aug. 27, 2013, 6 pages (3 pages of English Translation and 3 pages of Official copy).
Rosenschein et al., "Shock-Wave Thrombus Ablation, a New Method for Noninvasive Mechanical Thrombolysis", The American Journal of Cardiology, vol. 70, Nov. 15, 1992, pp. 1358-1361.
Zhong et al., "Transient Oscillation of Cavitation Bubbles Near Stone Surface During Electohydraulic Lithotripsy", Journal of Endourology, vol. 11, No. 1, Feb. 1997, pp. 55-61.
Extended European Search Report (includes Supplementary European Search Report and Search Opinion) received for European Patent Application No. 09763640.1, mailed on Oct. 10, 2013, 5 pages.
Final Office Action received for U.S. Appl. No. 12/482,995, mailed on Feb. 20, 2014, 11 pages.
Non-Final Office Action received for U.S. Appl. No. 12/501,619, mailed on Jan. 28, 2014, 10 pages.
Non-Final Office Action received for U.S. Appl. No. 13/049,199, mailed on Feb. 4, 2014, 8 pages.
Advisory Action received for U.S. Appl. No. 13/267,383, mailed on Jan. 6, 2014, 4 pages.
Notice of Allowance received for U.S. Appl. No. 14/061,554, mailed on Apr. 25, 2014, 8 pages.
Non-Final Office Action received for U.S. Appl. No. 14/061,554, mailed on Mar. 12, 2014, 14 pages.
Final Office Action received for U.S. Appl. No. 13/267,383, mailed on Oct. 25, 2013, 8 pages.
International Search Report and Written Opinion received for PCT Patent Application No. PCT/US2013/055431, mailed on Nov. 12, 2013, 9 pages.
International Search Report and Written Opinion received for PCT Patent Application No. PCT/US2013/059533, mailed on Nov. 7, 2013, 14 pages.
International Search Report and Written Opinion received for PCT Patent Application No. PCT/US2013/039987, mailed on Sep. 23, 2013, 15 pages.
International Search Report and Written Opinion received for PCT Patent Application No. PCT/US2013/048277, mailed on Oct. 2, 2013, 14 pages.
Adams, John M., U.S. Appl. No. 14/218,858, filed Mar. 18, 2014, titled "Shockwave Catheter System with Energy Control" 24 pages (Copy not attached).

Non Final Office Action received for U.S. Appl. No. 14/079,463, mailed on Mar. 4, 2014, 9 pages.
Notice of Allowance received for U.S. Appl. No. 14/079,463, mailed on Apr. 1, 2014, 5 pages.
Non Final Office Action received for U.S. Appl. No. 12/482,995, mailed on Aug. 13, 2014, 10 pages.
Final Office Action received for U.S. Appl. No. 13/049,199 mailed on Aug. 11, 2014, 8 pages.
Notice of Allowance received for U.S. Appl. No. 13/831,543, mailed on Oct. 8, 2014, 14 pages.
Non-Final Office Action received for U.S. Appl. No. 14/271,276, mailed on Aug. 4, 2014, 7 pages.
Non-Final Office Action received for U.S. Appl. No. 14/271,342, mailed on Sep. 2, 2014, 6 pages.
Notice of Acceptance Received for Australian Patent Application No. 2009257368, mailed on Aug. 28, 2014, 2 pages.
Office Action received for Australian Patent Application No. 2009257368, issued on Apr. 28, 2014, 4 pages.
Office Action Received for Japanese Patent Application No. 2011-513694, mailed on Jun. 10, 2014, 2 pages of Official Copy only (See Communication under 37 CFR § 1.98(a) (3)).
Cleveland et al., "The Physics of Shock Wave Lithotripsy", Extracorporeal Shock Wave Lithotripsy Part IV, Chapter 38, 2012, pp. 317-332.
Connors et al., "Renal Nerves Mediate Changes in Contralateral Renal Blood Flow after Extracorporeal Shockwave Lithotripsy", Nephron Physiol, vol. 95, 2003, pp. 67-75.
Doug Hakala, Unpublished U.S. Appl. No. 14/515,130, filed Oct. 15, 2014, titled "Low Profile Electrodes for an Angioplasty Shock Wave Catheter", Copy Not Attached.
Gambihler et al., "Permeabilization of the Plasma Membrane of LI210 Mouse Leukemia Cells Using Lithotripter Shock Waves", The Journal of Membrane Biology, vol. 141, 1994, pp. 267-275.
Grassi et al., "Novel Antihypertensive Therapies: Renal Sympathetic Nerve Ablation and Carotid Baroreceptor Stimulation", Curr Hypertens Rep vol. 14, 2012, pp. 567-572.
Kodama et al., "Shock wave-mediated molecular delivery into cells", Biochimica et Biophysica Acta vol. 1542, 2002, pp. 186-194.
Lauer et al., "Shock wave permeabilization as a new gene transfer method", Gene Therapy vol. 4, 1997, pp. 710-715.
Non Final Office Action received for U.S. Appl. No. 13/465,264, mailed on Oct. 29, 2014, 13 pages.
Non Final Office Action received for U.S. Appl. No. 13/646,570, mailed on Oct. 29, 2014, 10 pages.
Non-Final Office Action received for U.S. Appl. No. 13/646,583, mailed on Oct. 31, 2014, 8 pages.
Written Opinon received for PCT Patent Application No. PCT/US2009/047070, mailed on Jan. 19, 2010, 5 pages.
International Preliminary Report on Patentability received for PCT Patent Application No. PCT/US2009/047070, mailed on Dec. 23, 2010, 7 pages.

\* cited by examiner

FIG. 10A
(PRIOR ART)
FIG. 10B
(PRIOR ART)
FIG. 10C
(PRIOR ART)
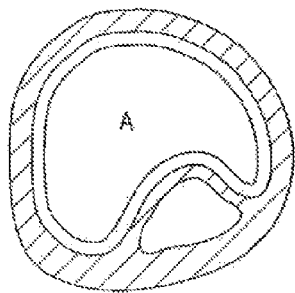 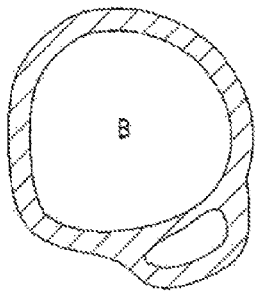 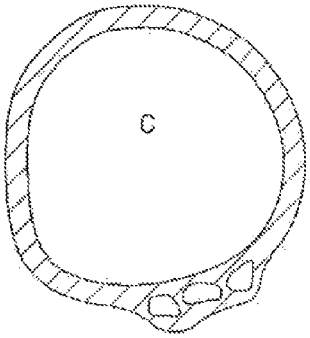
FIG. 11
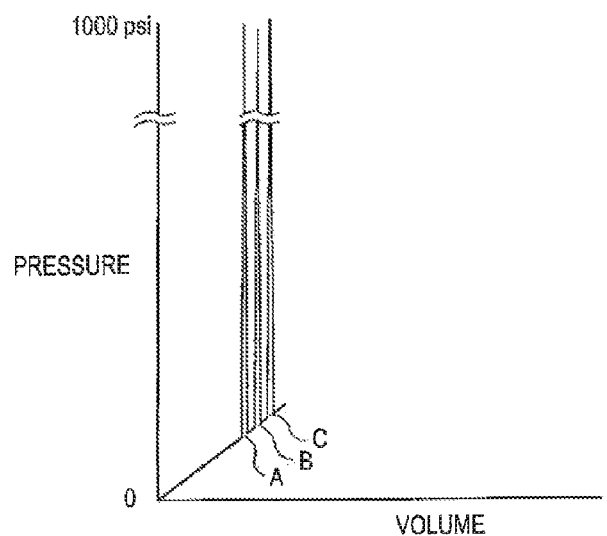
FIG. 11A
FIG. 11B
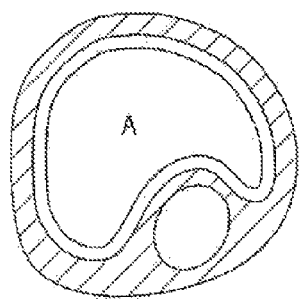 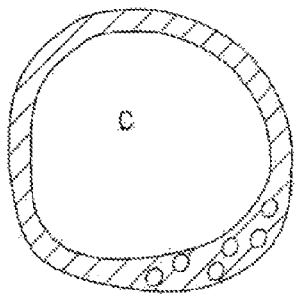

US 9,180,280 B2

DRUG DELIVERY SHOCKWAVE BALLOON CATHETER SYSTEM

PRIORITY CLAIM

The present application claims the benefit of U.S. Provisional Patent Application Ser. No. 61/111,196, filed Nov. 4, 2008, which application is incorporated herein by reference in its entirety.

BACKGROUND OF THE INVENTION

The present invention relates to a treatment system for percutaneous coronary angioplasty or peripheral angioplasty in which a dilation catheter is used to cross a lesion in order to dilate the lesion and restore normal blood flow in the artery. It is particularly useful when the lesion is a calcified lesion in the wall of the artery. Calcified lesions require high pressures (sometimes as high as 10-15 atmospheres) to break the calcified plaque and push it back into the vessel wall. With such pressures comes trauma to the vessel wall which can contribute to vessel rebound, dissection, thrombus formation, and a high level of restenosis. Non-concentric calcified lesions can result in undue stress to the free wall of the vessel when exposed to high pressures. An angioplasty balloon when inflated to high pressures can have a specific maximum diameter to which it will expand but the opening in the vessel under a concentric lesion will typically be much smaller. As the pressure is increased to open the passage way for blood the balloon will be confined to the size of the open in the calcified lesion (before it is broken open). As the pressure builds a tremendous amount of energy is stored in the balloon until the calcified lesion breaks or cracks. That energy is then released and results in the rapid expansion of the balloon to its maximum dimension and may stress and injure the vessel walls. Anti-proliferative drugs such as Paclitaxel delivered to the site of balloon expansion or stent deployment is known to reduce the response of the vessel to the injury or the stent. Such drugs are currently coated on the stent surface and provide long term deployment to prevent restenosis due to cell proliferation.

SUMMARY OF THE INVENTION

In one embodiment, a catheter comprises an elongated carrier, a balloon carried by the carrier in sealed relation thereto, the balloon having an outer surface and being arranged to receive a fluid therein that inflates the balloon, and a shock wave generator within the balloon that forms mechanical shock waves within the balloon. The catheter further includes a medicinal agent carried on the outer surface of the balloon. The medicinal agent is releasable from the balloon by the shock waves.

The medicinal agent may be in the form of a plurality of microspheres. The microspheres may have a diameter of between about 2 microns and about 100 microns.

Alternatively, the medicinal agent may in the form of a plurality of microcapsules having a drug therein, wherein the drug is releasable from the microcapsules by the shock waves. The microcapsules may have a diameter of between about 2 microns and about 100 microns. The microcapsules may be arranged to crack open upon exposure to the shock waves. The microcapsules may be formed of a polymer, a starch, or glucose.

The medicinal agent may still alternatively be in the form of a layer of a drug bonded to the balloon outer surface.

According to another embodiment, a method comprises the step of providing a catheter having an elongated carrier and a balloon carried by the carrier in sealed relation thereto. The balloon has an outer surface. The method further comprises the steps of applying a medicinal agent to the outer surface of the balloon, inflating the balloon with a liquid, and producing mechanical shock waves within the balloon to release the medicinal agent from the balloon outer surface.

The applying step may include providing the medicinal agent in the form of a plurality of microspheres. The microspheres may be formed to have a diameter of between about 2 microns and about 100 microns.

The applying step may alternatively include providing the medicinal agent in the form of a plurality of microcapsules having a drug therein, wherein the drug is releasable from the microcapsules by the shock waves. The microcapsules may be formed to have a diameter of between about 2 microns and about 100 microns. The mechanical shocks waves are preferably provided with sufficient energy to cause the microcapsules to crack open to release the drug. The microcapsules are formed of a polymer, a starch, or glucose.

The applying step may further alternatively include providing the medicinal agent in the form of a layer of a drug bonded to the balloon outer surface.

BRIEF DESCRIPTION OF THE DRAWINGS

The features of the present invention which are believed to be novel are set forth with particularity in the appended claims. The various embodiments of the invention, together with representative features and advantages thereof, may best be understood by making reference to the following description taken in conjunction with the accompanying drawings, in the several figures of which like reference numerals identify identical elements, and wherein:

FIG. 10A is a sectional view of a balloon expanding freely within a vessel;

FIG. 10B is a sectional view of a balloon constrained to the point of breaking in a vessel;

FIG. 10C is a sectional view of a balloon after breaking within the vessel;

FIG. 11 is a pressure volume curve showing the various stages in the breaking of a calcified lesion with shock waves according to an embodiment of the invention.

FIG. 11A is a sectional view showing a compliant balloon within a vessel;

FIG. 11B is a sectional view showing pulverized calcification on a vessel wall;

DETAILED DESCRIPTION OF THE INVENTION

Figure 1:
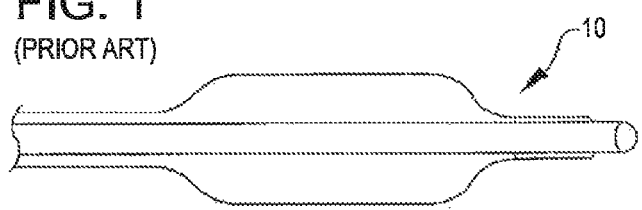
FIG. 1 is a view of the therapeutic end of a typical prior art over-the-wire angioplasty balloon catheter.

FIG. 1 is a view of the therapeutic end of a typical prior art over-the-wire angioplasty balloon catheter 10. Such catheters are usually non-complaint with a fixed maximum dimension when expanded with a fluid such as saline.

Figure 2:
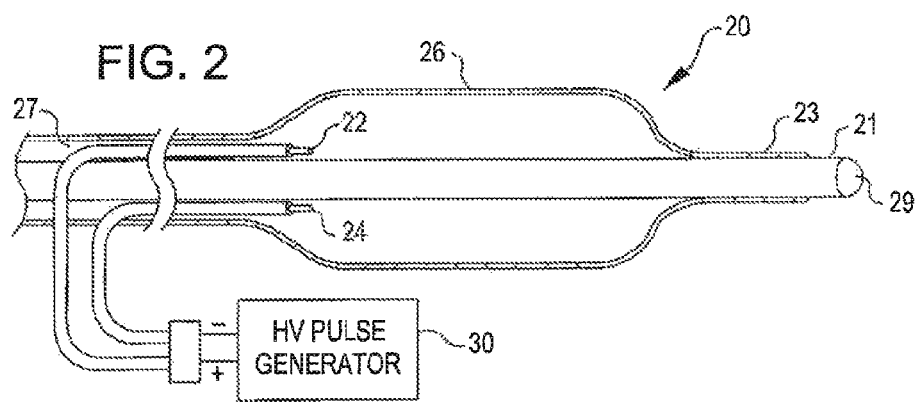
FIG. 2 is a side view of a dilating angioplasty balloon catheter with two electrodes within the balloon attached to a source of high voltage pulses according to one embodiment of the invention.

FIG. 2 is a view of a dilating angioplasty balloon catheter 20 according to an embodiment of the invention. The catheter 20 includes an elongated carrier, such as a hollow sheath 21, and a dilating balloon 26 formed about the sheath 21 in sealed relation thereto at a seal 23. The balloon 26 forms an annular channel 27 about the sheath 21 through which fluid, such as saline, may be admitted into the balloon to inflate the balloon. The channel 27 further permits the balloon 26 to be provided with two electrodes 22 and 24 within the fluid filled balloon 26. The electrodes 22 and 24 are attached to a source of high voltage pulses 30. The electrodes 22 and 24 are formed of metal, such as stainless steel, and are placed a controlled distance apart to allow a reproducible arc for a given voltage and current. The electrical arcs between electrodes 22 and 24 in the fluid are used to generate shock waves in the fluid. The variable high voltage pulse generator 30 is used to deliver a stream of pulses to the electrodes 22 and 24 to create a stream of shock waves within the balloon 26 and within the artery being treated (not shown). The magnitude of the shock waves can be controlled by controlling the magnitude of the pulsed voltage, the current, the duration and repetition rate. The insulating nature of the balloon 26 protects the patient from electrical shocks.

The balloon 26 may be filled with water or saline in order to gently fix the balloon in the walls of the artery in the direct proximity with the calcified lesion. The fluid may also contain an x-ray contrast to permit fluoroscopic viewing the catheter during use. The carrier 21 includes a lumen 29 through which a guidewire (not shown) may be inserted to guide the catheter into position. Once positioned the physician or operator can start with low energy shock waves and increase the energy as needed to crack the calcified plaque. Such shockwaves will be conducted through the fluid, through the balloon, through the blood and vessel wall to the calcified lesion where the energy will break the hardened plaque without the application of excessive pressure by the balloon on the walls of the artery.

Figure 3:
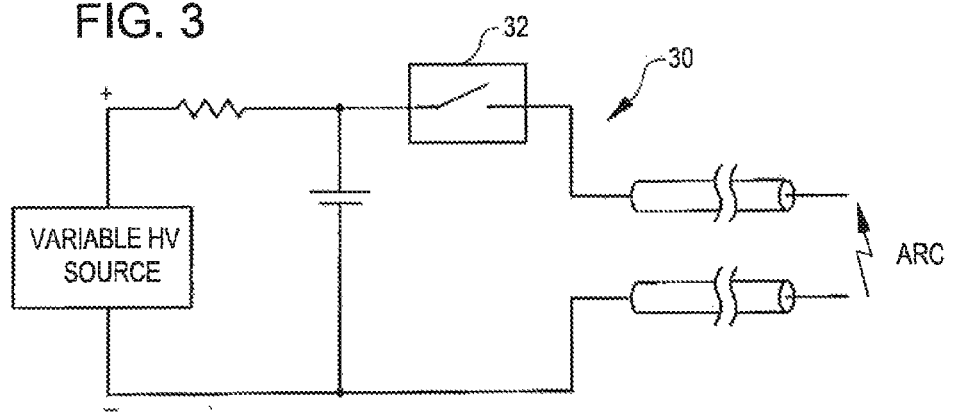
FIG. 3 is a schematic of a high voltage pulse generator.
Figure 3A:
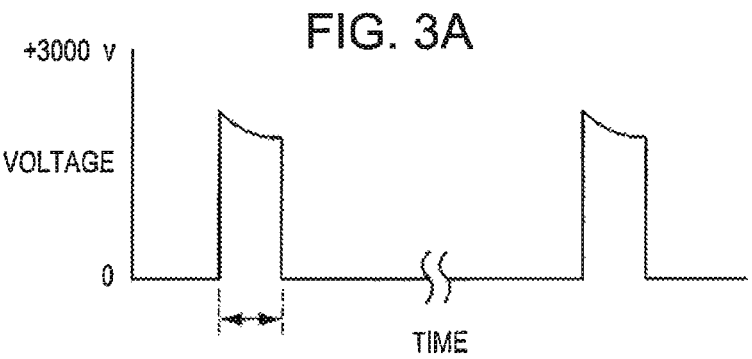
FIG. 3A shows voltage pulses that may be obtained with the generator of FIG. 3.

FIG. 3 is a schematic of the high voltage pulse generator 30. FIG. 3A shows a resulting waveform. The voltage needed will depend on the gap between the electrodes and generally 100 to 3000 volts. The high voltage switch 32 can be set to control the duration of the pulse. The pulse duration will depend on the surface area of the electrodes 22 and 24 and needs to be sufficient to generate a gas bubble at the surface of the electrode causing a plasma arc of electric current to jump the bubble and create a rapidly expanding and collapsing bubble, which creates the mechanical shock wave in the balloon. Such shock waves can be as short as a few microseconds.

Figure 4:
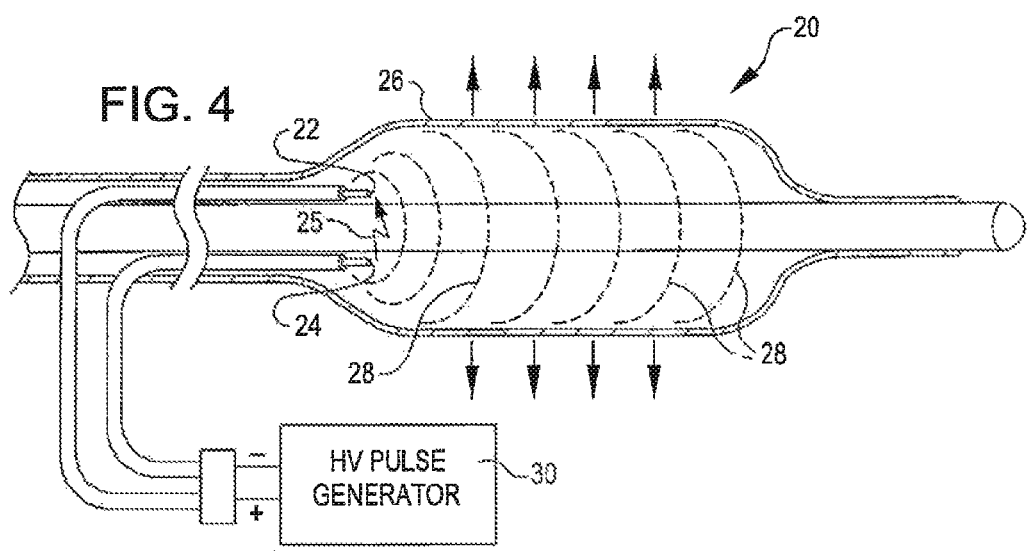
FIG. 4 is a side view of the catheter of FIG. 2 showing an arc between the electrodes and simulations of the shock wave flow.

FIG. 4 is a cross sectional view of the shockwave catheter 20 showing an arc 25 between the electrodes 22 and 24 and simulations of the shock wave flow 28. The shock wave 28 will radiate out from the electrodes 22 and 24 in all directions and will travel through the balloon 26 to the vessel where it will break the calcified lesion into smaller pieces.

Figure 5:
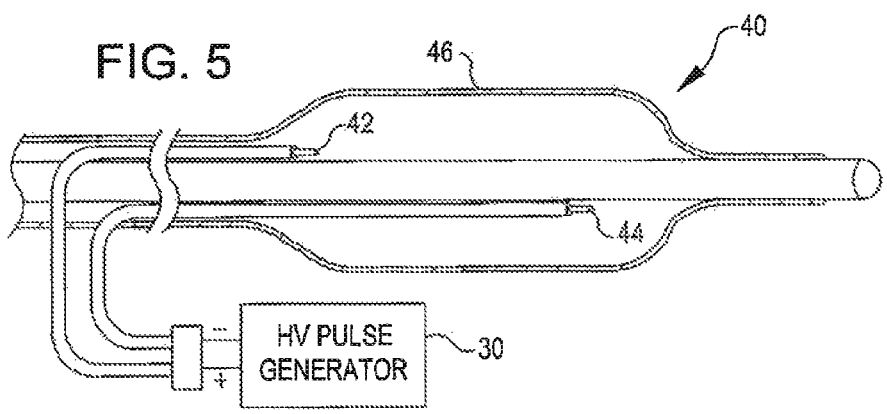
FIG. 5 is a side view of a dilating catheter with insulated electrodes within the balloon and displaced along the length of the balloon according to another embodiment of the invention.

FIG. 5 shows another dilating catheter 40. It has insulated electrodes 42 and 44 within the balloon 46 displaced along the length of the balloon 46.

Figure 6:
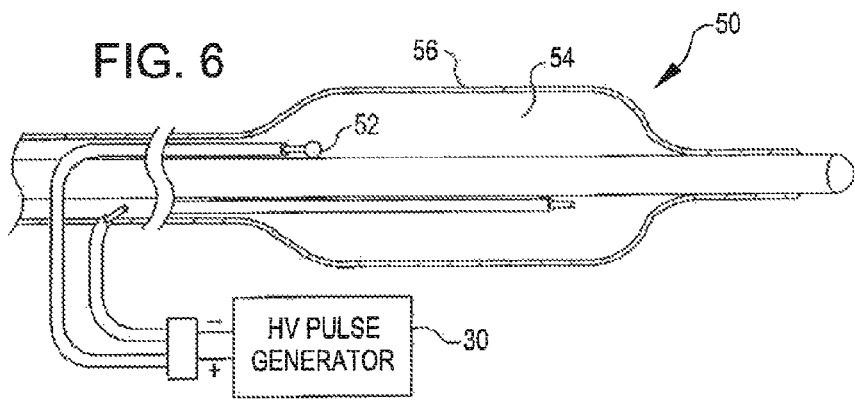
FIG. 6 is a side view of a dilating catheter with insulated electrodes within the balloon displaced with a single pole in the balloon and a second being the ionic fluid inside the balloon according to a further embodiment of the invention.

FIG. 6 shows a dilating catheter 50 with an insulated electrode 52 within the balloon 56. The electrode is a single electrode pole in the balloon, a second pole being the ionic fluid 54 inside the balloon. This unipolar configuration uses the ionic fluid as the other electrical pole and permits a smaller balloon and catheter design for low profile balloons. The ionic fluid is connected electrically to the HV pulse generator 30.

Figure 7:
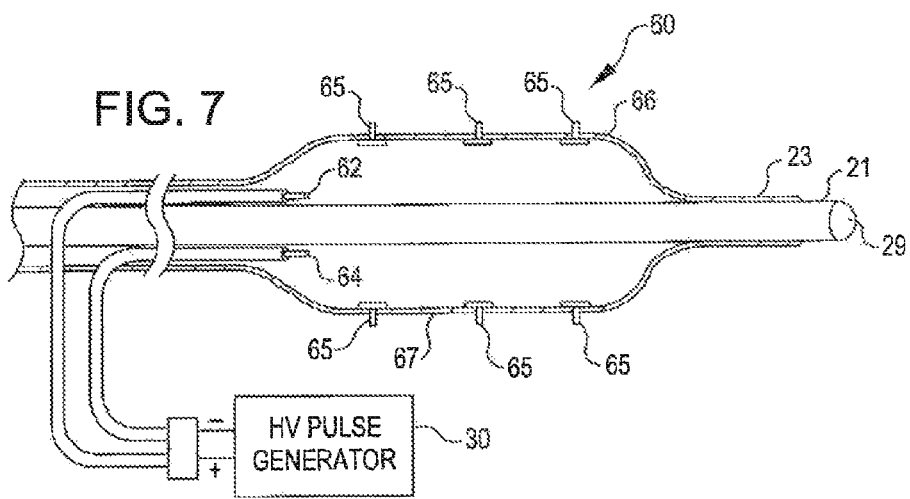
FIG. 7 is a side view of a dilating catheter with insulated electrodes within the balloon and studs to reach the calcification according to a still further embodiment of the invention.

FIG. 7 is another dilating 60 catheter with electrodes 62 and 64 within the balloon 66 and studs 65 to reach the calcification. The studs 65 form mechanical stress risers on the balloon surface 67 and are designed to mechanically conduct the shock wave through the intimal layer of tissue of the vessel and deliver it directly to the calcified lesion.

Figure 8:
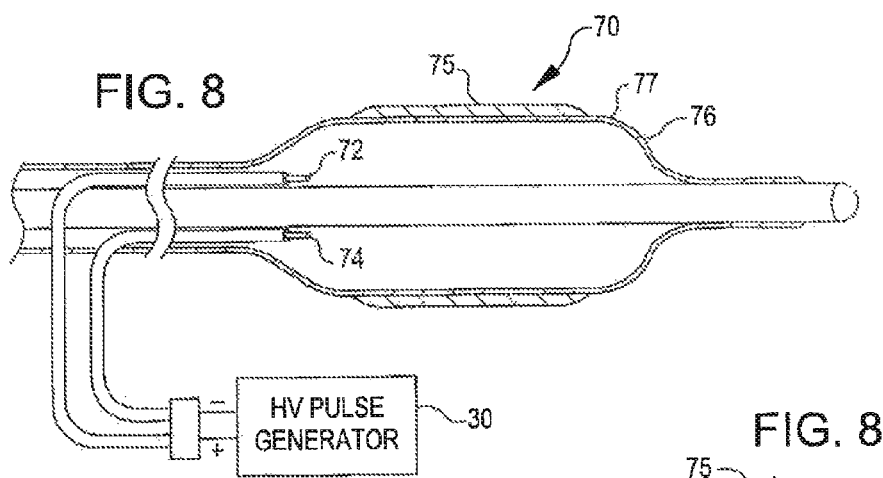
FIG. 8 is a side view of a dilating catheter with insulated electrodes within the balloon with raised ribs on the balloon according to still another embodiment of the invention.
Figure 8A:
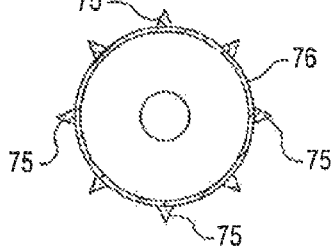
FIG. 8A is a front view of the catheter of FIG. 8.

FIG. 8 is another dilating catheter 70 with electrodes 72 and 74 within the balloon 76 and with raised ribs 75 on the surface 77 of the balloon 76. The raised ribs 75 (best seen in FIG. 8A) form stress risers that will focus the shockwave energy to linear regions of the calcified plaque.

Figure 9:
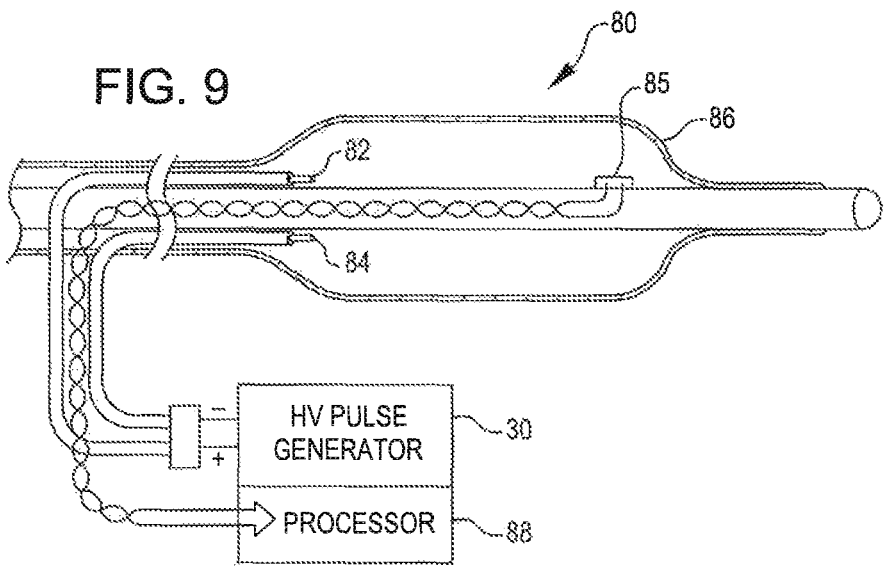
FIG. 9 is a side view of a dilating catheter with insulated electrodes within the balloon and a sensor to detect reflected signals according to a further embodiment of the invention.

FIG. 9 is a further dilating catheter 80 with electrodes 82 and 84 within the balloon 86. The catheter 80 further includes a sensor 85 to detect reflected signals. Reflected signals from the calcified plaque can be processed by a processor 88 to determine quality of the calcification and quality of pulverization of the lesion.

Figure 10:
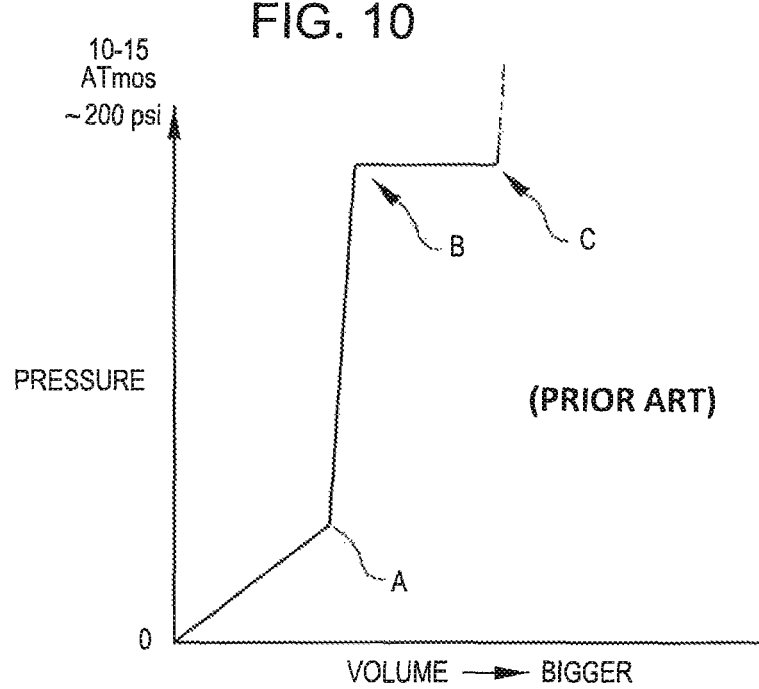
FIG. 10 is a pressure volume curve of a prior art balloon breaking a calcified lesion.

FIG. 10 is a pressure volume curve of a prior art balloon breaking a calcified lesion. FIG. 10B shows the build up of energy within the balloon (region A to B) and FIG. 10C shows the release of the energy (region B to C) when the calcification breaks. At region C the artery is expanded to the maximum dimension of the balloon. Such a dimension can lead to injury to the vessel walls. FIG. 10A shows the initial inflation of the balloon.

FIG. 11 is a pressure volume curve showing the various stages in the breaking of a calcified lesion with shock waves according to the embodiment. The balloon is expanded with a saline fluid and can be expanded to fit snugly to the vessel wall (Region A) (FIG. 11A) but this is not a requirement. As the High Voltage pulses generate shock waves (Region B and C) extremely high pressures, extremely short in duration will chip away the calcified lesion slowly and controllably expanding the opening in the vessel to allow blood to flow un-obstructed (FIG. 11B).

Figure 12:
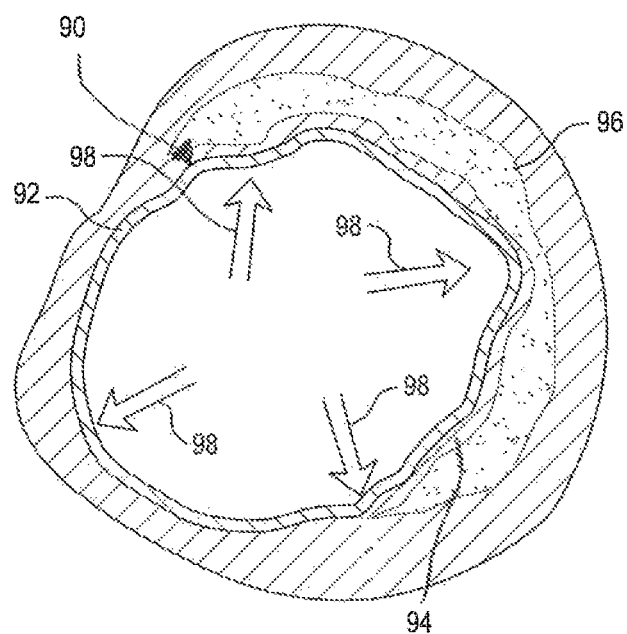
FIG. 12 illustrates shock waves delivered through the balloon wall and endothelium to a calcified lesion.

FIG. 12 shows, in a cutaway view, shock waves 98 delivered in all directions through the wall 92 of a saline filled balloon 90 and intima 94 to a calcified lesion 96. The shock waves 98 pulverize the lesion 96. The balloon wall 92 may be formed of non-compliant or compliant material to contact the intima 94.

Figure 13:
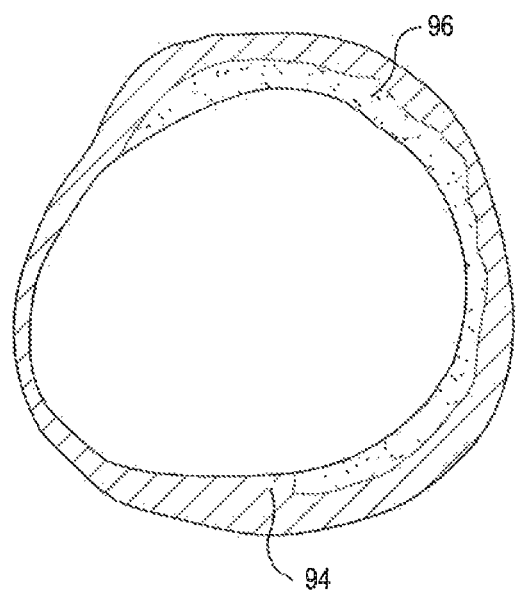
FIG. 13 shows calcified plaque pulverized and smooth a endothelium restored by the expanded balloon after pulverization.

FIG. 13 shows calcified plaque 96 pulverized by the shock waves. The intima 94 is smoothed and restored after the expanded balloon (not shown) has pulverized and reshaped the plaque into the vessel wall.

Figure 14:
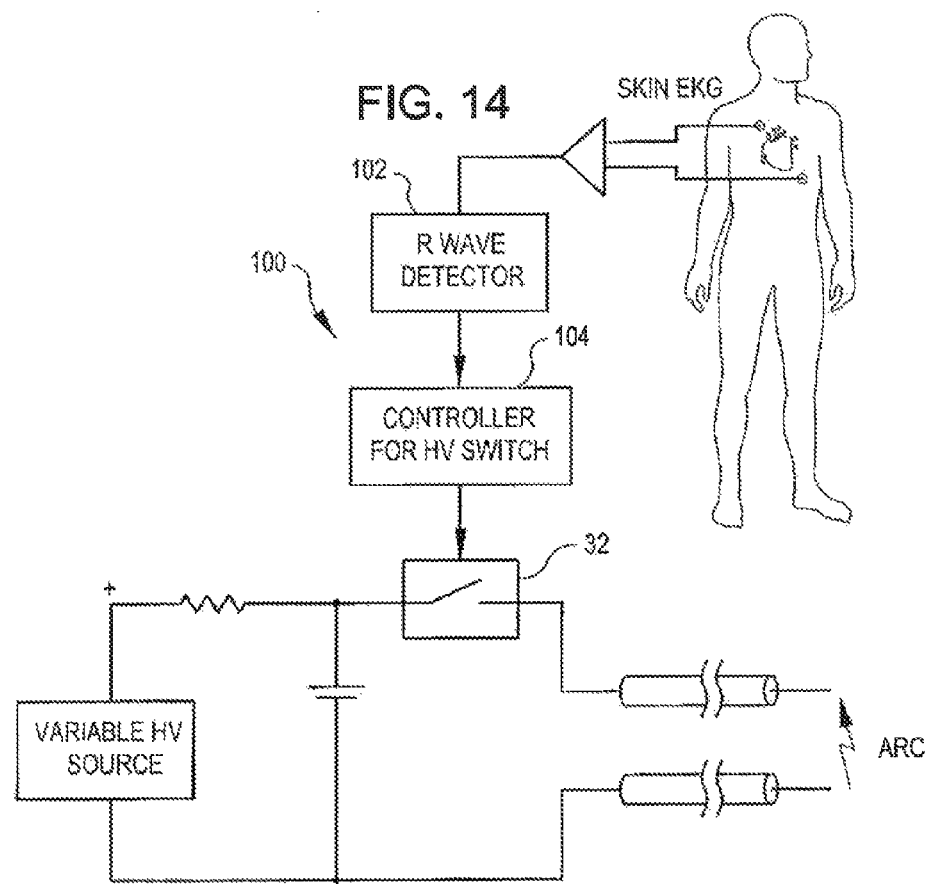
FIG. 14 is a schematic of a circuit that uses a surface EKG to synchronize the shock wave to the "R" wave for treating vessels near the heart.

FIG. 14 is a schematic of a circuit 100 that uses the generator circuit 30 of FIG. 3 and a surface EKG 102 to synchronize the shock wave to the "R" wave for treating vessels near the heart. The circuit 100 includes an R-wave detector 102 and a controller 104 to control the high voltage switch 32. Mechanical shocks can stimulate heart muscle and could lead to an arrhythmia. While it is unlikely that shockwaves of such, short duration as contemplated herein would stimulate the heart, by synchronizing the pulses (or bursts of pulses) with the R-wave, an additional degree of safety is provided when used on vessels of the heart or near the heart. While the balloon in the current drawings will provide an electrical isolation of the patient from the current, a device could be made in a non-balloon or non-isolated manner using blood as the fluid. In such a device, synchronization to the R-wave would significantly improve the safety against unwanted arrhythmias.

Figure 15:
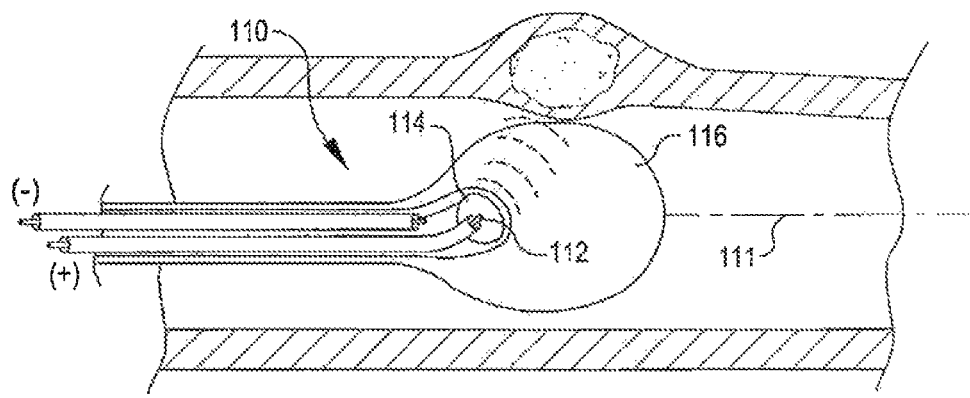
FIG. 15 is a side view, partly cut away, of a dilating catheter with a parabolic reflector acting as one electrode and provides a focused shock wave inside a fluid filled compliant balloon.

FIG. 15 shows a still further dilation catheter 110 wherein a shock wave is focused with a parabolic reflector 114 acting as one electrode inside a fluid filled compliant balloon 116. The other electrode 112 is located at the coaxial center of the reflector 114. By using the reflector as one electrode, the shock wave can be focused and therefore pointed at an angle (45 degrees, for example) off the center line 111 of the catheter artery. In this configuration, the other electrode 112 will be designed to be at the coaxial center of the reflector and designed to arc to the reflector 114 through the fluid. The catheter can be rotated if needed to break hard plaque as it rotates and delivers shockwaves.

Figure 16:
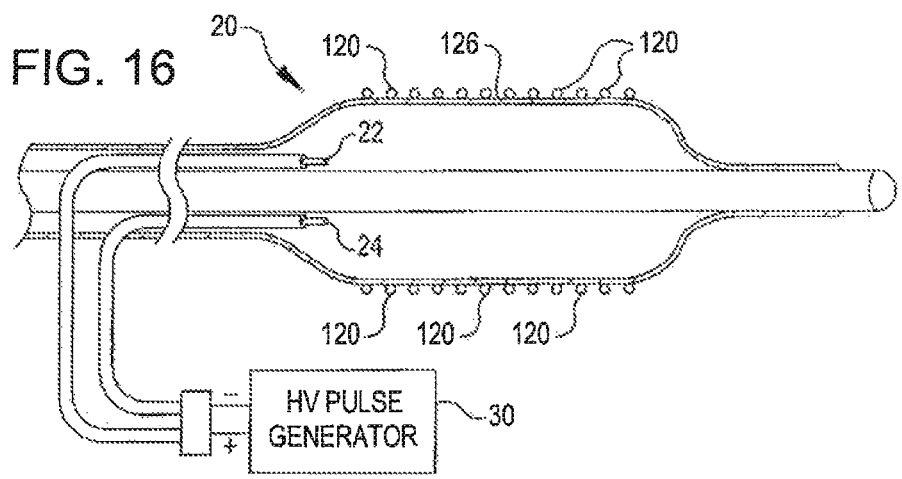
FIG. 16 is a shockwave angioplasty balloon similar to FIG. 2 with micro-balloons or microspheres filled with a drug on the surface of the balloon.

FIG. 16 shows a shock wave balloon 126 similar to FIG. 2 with microspheres or microcapsules 120 attached to the surface. Such micro spheres may contain an antiproliferative drug such as Paclitaxel, Serolimus or Evrolimus or other similar drug. The spheres may be designed to be rigid and resist breaking when exposed to normal balloon inflation pressures of several atmospheres. However, when exposed to high pressure shock waves, the microspheres will break and release the drug contained within. Shockwaves delivered from such a balloon have the added advantage of creating a permeable cell wall membrane which aides in the transfer of the released drug to the walls of the vessel. Such drugs are known to reduce the restenosis rate in vessels treated. These micro-encapsulations can range in size typically from 2 to 100 microns in diameter although the size is not critical if they are small relative to the balloon size. The material can be a rigid polymer, a starch, glucose or any number of materials chosen to crack when exposed to shock waves and resist cracking when exposed to normal pressures of an angioplasty dilation procedure.

Figure 17:
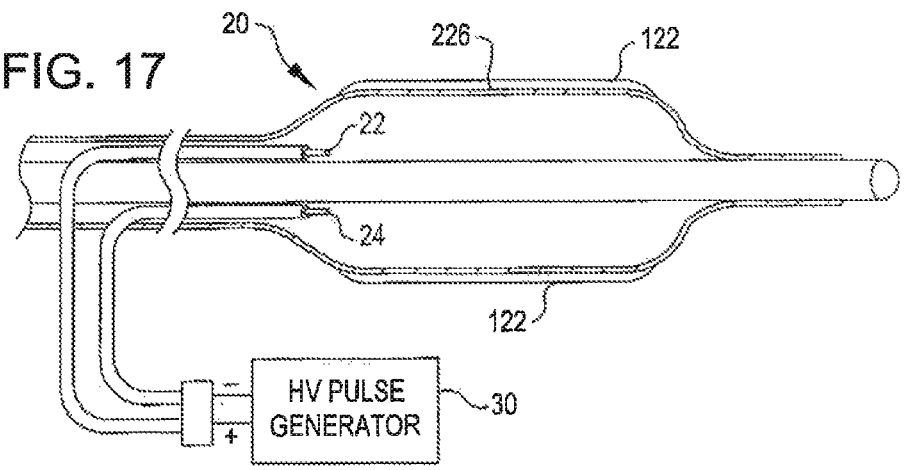
FIG. 17 is a layered shockwave balloon similar to FIG. 2 with an added layer of drug bonded to the balloon.

FIG. 17 is a layered shockwave balloon 226 similar to FIG. 2 with an added layer 122 of drug chemically bonded to the balloon. The drug is released from its bond to the balloon material by the mechanical force of a shockwave. Thus the drug (paclitaxel for example) will be released at the site of a lesion while the lesion is being expanded with the predilitation balloon. As with the micro-encapsulated drug the shock waves from the balloon can also create a permeable cell wall membrane aiding in the drug uptake in the vessel wall.

While particular embodiments of the present invention have been shown and described, modifications may be made. It is therefore intended in the appended claims to cover all such changes and modifications which fall within the true spirit and scope of the invention as defined by those claims.

What is claimed is:

1. A catheter comprising:
   an elongated carrier;
   a balloon carried by the elongated carrier in sealed relation thereto, the balloon having an outer surface and being arranged to receive fluid therein that inflates the balloon;
   a shock wave generator including a pair of electrodes located within the balloon, said pair of electrodes configured so that when a high voltage pulse is delivered thereto, a plasma arc is created which in turn creates a mechanical shock wave within the balloon; and
   a medicinal agent attached to the outer surface of the balloon, the medicinal agent being releasable from the outer surface of the balloon in response to the shock wave created within the balloon,
   wherein, the outer surface of the balloon remains sealed both during and after the creation of the shock wave and the release of the medicinal agent from the outer surface of the balloon.

2. The catheter of claim 1, wherein the medicinal agent is contained within a plurality of microspheres attached to the outer surface of the balloon.

3. The catheter of claim 2, wherein the plurality of microspheres have a diameter of between about 2 microns and about 100 microns.

4. The catheter of claim 1, wherein the medicinal agent is contained within a plurality of microcapsules attached to the outer surface of the balloon, wherein the medicinal agent is releasable from the plurality of microcapsules in response to the shock wave.

5. The catheter of claim 4, wherein the plurality of microcapsules have a diameter of between about 2 microns and about 100 microns.

6. The catheter of claim 4, wherein the plurality of microcapsules are arranged to crack open in response to the shock wave.

7. The catheter of claim 4, wherein the plurality of microcapsules comprise a polymer.

8. The catheter of claim 4, wherein the plurality of microcapsules comprise a starch.

9. The catheter of claim 4, wherein the plurality of microcapsules comprise glucose.

10. The catheter of claim 1, wherein the medicinal agent is in the form of a layer of a drug bonded to the balloon outer surface.

11. The catheter of claim 1, wherein the balloon is a dilation balloon.

12. The catheter of claim 1, wherein the elongated carrier includes a guide wire lumen.

13. A method comprising:
   providing a catheter comprising an elongated carrier, a balloon carried by the elongated carrier in sealed relation thereto, a shock wave generator within the balloon, a medicinal agent attached to an outer surface of the balloon,
   inserting the catheter into a blood vessel to be treated;
   inflating the balloon with a liquid; and supplying a high voltage pulse to a pair of electrodes located within the balloon to produce a plasma arc which in turn creates a mechanical shock wave within the balloon to release the medicinal agent from the outer surface of the balloon with the outer surface of the balloon remaining sealed both during and after the creation of the shock wave and the release of the medicinal agent from the outer surface of the balloon.

14. The method of claim 13, wherein the medicinal agent is contained within a plurality of microspheres.

15. The method of claim 14, wherein the plurality of microspheres have a diameter of between about 2 microns and about 100 microns.

16. The method of claim 13, wherein the medicinal agent is contained within a plurality of microcapsules having a drug therein, wherein the drug is releasable from the plurality of microcapsules in response to the shock wave.

17. The method of claim 16, wherein the plurality of microcapsules have a diameter of between about 2 microns and about 100 microns.

18. The method of claim 16, wherein the mechanical shock wave generates sufficient energy to cause the plurality of microcapsules to crack open to release the drug.

19. The method of claim 16, wherein the plurality of microcapsules comprise a polymer.

20. The method of claim 16, wherein the plurality of microcapsules comprise a starch.

21. The method of claim 16, wherein the plurality of microcapsules comprise glucose.

22. The method of claim 13, wherein the medicinal agent is in the form of a layer of a drug bonded to the balloon outer surface.

23. The method of claim 13, further including the step of placing the balloon into a vessel or artery before inflating the balloon, wherein the balloon is a dilation balloon, and wherein the inflating step includes dilating the vessel or artery.

* * * * *